US010966384B2

(12) United States Patent
Mills et al.

(10) Patent No.: US 10,966,384 B2
(45) Date of Patent: Apr. 6, 2021

(54) COTTON VARIETY FM 2498GLT

(71) Applicant: BASF Agricultural Solutions Seed US LLC, Research Triangle Park, NC (US)

(72) Inventors: Cory Mills, Research Triangle Park, NC (US); Anna Hall, Research Triangle Park, NC (US)

(73) Assignee: BASF AGRICULTURAL SOLUTIONS SEED US LLC, Research Triangle Park, NC (US)

( * ) Notice: Subject to any disclaimer, the term of this patent is extended or adjusted under 35 U.S.C. 154(b) by 22 days.

(21) Appl. No.: 16/405,254

(22) Filed: May 7, 2019

(65) Prior Publication Data

US 2019/0261590 A1 Aug. 29, 2019

Related U.S. Application Data

(63) Continuation-in-part of application No. 16/279,791, filed on Dec. 19, 2019, now abandoned.

(60) Provisional application No. 62/632,023, filed on Feb. 19, 2018.

(51) Int. Cl.
*A01H 5/10* (2018.01)
*A01H 6/60* (2018.01)
(52) U.S. Cl.
CPC ............... *A01H 5/10* (2013.01); *A01H 6/604* (2018.05)
(58) Field of Classification Search
None
See application file for complete search history.

(56) References Cited

U.S. PATENT DOCUMENTS

| 6,818,807 B2 | 11/2004 | Trolinder et al. |
| 2009/0049564 A1 | 2/2009 | Burdett |
| 2015/0257349 A1* | 9/2015 | Robinson .................. A01H 5/10 800/263 |

FOREIGN PATENT DOCUMENTS

| EP | 0270355 A2 | 6/1988 |
| WO | 0071733 A1 | 11/2000 |

OTHER PUBLICATIONS

"Objective description of Variety Cotton (*Gossypium* spp.)", U.S. Department of Agricultural Marketing Service Science and Technology Plant Variety Protection Office, 2015, 4 pages.
Briggs, et al., "Introduction to Plant Breeding", Reinhold Publishing Corporation, 1967, 3 pages.
Piet Stam, "Marker-assisted introgression: speed at any cost?", Proceedings of the Eucarpia Meeting on Leafy Vegetable Genetics and Breeding, Noordwijkerhout, The Netherlands, ed. Van Hintum, et al., Mar. 19-21, 2003, pp. 117-124.
Pisanu, et al., "Yield and Biometric Characteristics of 9 Clones Selected from the Population of "Spinoso Sardo" Artichokes", ISHS Acta Horticulturae 660: V International Congress on Artichoke, 2004, pp. 83-89.
Sakhanokho, et al., "Induction of Somatic embryogenesis and Plant Regeneration in Select Georgia and Pee Dee Cotton Lines", Crop Science, vol. 44, Issue 6, 2004, pp. 2199-2205.
Vos, et al., "AFLP: a new technique for DNA fingerprinting", Nucleic Acids Research, vol. 23, Issue 21, 1995, pp. 4407-4414.

* cited by examiner

*Primary Examiner* — Charles Logsdon
(74) *Attorney, Agent, or Firm* — Arent Fox LLP

(57) ABSTRACT

The disclosure provides a new cotton variety FM 2498GLT. The disclosure relates to seeds, plants, plant cells, plant tissue, harvested products and cotton lint as well as to hybrid cotton plants and seeds obtained by repeatedly crossing plants of variety FM 2498GLT with other plants. The disclosure also relates to plants of variety FM 2498 reproduced by vegetative methods, including but not limited to tissue culture of regenerable cells or tissue from cotton variety FM 2498GLT.

19 Claims, No Drawings

COTTON VARIETY FM 2498GLT

CROSS REFERENCE TO RELATED APPLICATION

This application is a continuation-in-part of U.S. patent application Ser. No. 16/279,791, filed on Feb. 19, 2019, which claims priority to U.S. Provisional Patent Application No. 62/632,023 filed on Feb. 19, 2018, each of which is hereby incorporated by reference in its entirety.

FIELD OF THE DISCLOSURE

The disclosure relates to the field of plant breeding, and more specifically, to cotton variety FM 2498GLT. The disclosure further relates to vegetative reproduction of cotton variety FM 2498GLT, methods for tissue culture of cotton variety FM 2498GLT, methods for regenerating a plant from such a tissue culture and to phenotypic variants of cotton variety FM 2498GLT. The disclosure also relates to progeny of cotton variety FM 2498GLT and the hybrid varieties obtained by crossing cotton variety FM 2498GLT as a parent line with plants of other varieties or parent lines.

BACKGROUND OF THE DISCLOSURE

Cotton is an important, fiber producing crop. Due to the importance of cotton to the textile industry, cotton breeders are increasingly seeking to obtain healthy, good yielding crops of excellent quality.

Cotton is commonly reproduced by self-pollination and fertilization. This type of sexual reproduction facilitates the preservation of plant and variety characteristics during breeding and seed production. The preservation of these characteristics is often important to plant breeders for producing cotton plants having desired traits. Other methods of producing cotton plants having desired traits are also used and include methods such as genetic transformation via *Agrobacterium* infection or direct transfer by microparticle bombardment (see, e.g., US 2009/0049564).

Due to environment, the complexity of the structure of genes and location of a gene in the genome, among other factors, it is difficult to predict the phenotypic expression of a particular genotype. In addition, a plant breeder may only apply his skills on the phenotype and not, or in a very limited way, on the level of the genotype. As a result, a particular plant breeder cannot breed the same variety twice using the same parents and the same methodology. Thus, a newly bred variety is an unexpected result of the breeding process. Indeed, each variety contains a unique combination of characteristics.

By carefully choosing the breeding parents, the breeding and selection methods, the testing layout and testing locations, the breeder may breed a particular variety type. In addition, a new variety may be tested in special comparative trials with other existing varieties in order to determine whether the new variety meets the required expectations.

SUMMARY OF THE VARIOUS ASPECTS OF THE DISCLOSURE

The disclosure provides for cotton variety FM 2498GLT, products thereof, and methods of using the same.

In one aspect, the disclosure provides a seed of cotton variety FM 2498GLT, wherein a representative sample of said seed will be deposited under ATCC Accession Number PTA 126942.

The disclosure also provides a plant grown from the seed of cotton variety FM 2498GLT and a plant part thereof. The disclosure also provides for a progeny of cotton variety FM 2498GLT. In another aspect, the disclosure provides a plant or a progeny retaining all or all but one, two, or three of the distinguishing characteristics or all or all but one, two, or three of the morphological and physiological characteristics of cotton variety FM 2498GLT and methods of producing that plant or progeny.

In one aspect, the disclosure provides a plant or a progeny having all the physiological and morphological characteristics of variety FM 2498GLT when grown under the same environmental conditions. In another aspect, the plant or progeny has all or all but one, two, or three of the physiological and morphological characteristics of cotton variety FM 2498GLT when measured under the same environmental conditions. In another aspect, the plant or progeny has all or all but one, two, or three of the physiological and morphological characteristics as listed in Table 1 for variety FM 2498GLT when measured under the same environmental conditions.

In another aspect, a plant of FM 2498GLT or a progeny thereof has at least 12, 13, or more of the following distinguishing characteristics when compared with Reference Variety FM 1911GLT as shown in Table 2: 1) stronger fiber; 2) coarser fiber (micronaire); 3) taller mature plant (from cotyledonary node to terminal); 4) a spreading plant habit; 5) an indeterminate growth; 6) longer length from cotyledonary node to $1^{st}$ fruiting branch; 7) higher gin turnout (stripped); and 8) more seeds per boll.

In another aspect, cotton variety FM 2498GLT contains a transgene which confers resistance to herbicides glyphosate and glufosinate, and for lepidopteran insect control, referred to in aggregate as the trait package GLYTOL® TWIN-LINK® (GLT).

In another aspect, the plant of cotton variety FM 2498GLT or a part thereof, or progeny thereof comprises resistance to *Xanthomonas axonopodis* (Bacterial Blight) Race 18, *Verticillium dahlia*, *Helicoverpa* spp. (Bollworm); *Spodoptera frugiperda* (Fall Armyworm), *Pectinophora gossypiella* (Pink Bollworm), and *Heliothis virescens* (Tobacco Bud Worm).

In another aspect, the disclosure provides for a plant part obtained from cotton variety FM 2498GLT, wherein said plant part is a leaf, a part of a leaf, pollen, an ovule, an embryo, a meristem, a petiole, a shoot or a part thereof, a stem or a part thereof, a root or a part thereof, a root tip, a seed, a part of a seed, a pod, a hypocotyl, cotyledon, a pistil, an anther, and a flower or a part thereof and the like. In another aspect, the plant part obtained from cotton variety FM 2498GLT is a cell or tissue culture.

The disclosure also provides for a cotton plant regenerated from the cell or tissue culture of cotton variety FM 2498GLT, wherein the regenerated plant has all of the physiological and morphological characteristics of cotton variety FM 2498GLT, when grown under the same environmental conditions, as well as methods for regenerating cotton variety FM 2498GLT.

The disclosure further provides a vegetatively propagated plant of variety FM 2498GLT having all or all but one, two, or three of the physiological and morphological characteristics of cotton variety FM 2498GLT, when grown under the same environmental conditions.

In another aspect, the disclosure provides for cotton lint or fiber produced by the plant of cotton variety FM 2498GLT. Also encompassed herein is the textile produced form the unique fiber of cotton variety FM 2498GLT.

The disclosure further provides a method of producing a commodity plant product (e.g., lint, cotton seed oil) comprising obtaining a plant of cotton variety FM 2498GLT or a part thereof and producing said commodity plant product therefrom.

Definitions

"Cotton" refers herein to plants of the species *Gossypium* spp.

A "seed of FM 2498GLT" refers to a cotton seed which can be grown into a plant of variety FM 2498GLT, wherein a representative sample of viable seed of said variety is to be deposited under ATCC Accession Number PTA 126942.

"Reference Variety for FM 2498GLT" refers herein to variety FM 1911GLT from BASF Agricultural Solutions Seed US LLC, which has been planted in a trial together with cotton variety FM 2498GLT. The characteristics of cotton variety FM 2498GLT were compared with the characteristics of variety FM 1911GLT as shown in Table 1. The distinguishing characteristics between cotton variety FM 2498GLT and the Reference Variety FM 1911GLT are shown in Table 2.

A plant having "all the physiological and morphological characteristics" of a referred-to-plant means a plant showing the physiological and morphological characteristics of the referred-to-plant when grown under the same environmental conditions, preferably in the same experiment or field; the referred-to-plant can be a plant from which it was derived; e.g., the progenitor plant, the parent, the recurrent parent, the plant used for tissue- or cell culture, etc. A physiological and morphological characteristic can be a numerical characteristic or a non-numerical characteristic. In one aspect, a plant has "all but one, two, or three of the physiological and morphological characteristics" of a referred-to-plant, or "all the physiological and morphological characteristics" of Table 1 or "all or all but one, two, or three of the physiological and morphological characteristics" of Table 1.

The physiological and/or morphological characteristics mentioned above are commonly evaluated at significance levels of 1%, 5%, or 10% if they are numerical (quantitative), or for having an identical degree (or type) if not numerical (not quantitative), if measured under the same environmental conditions.

"Distinguishing characteristics" or "distinguishing morphological and/or physiological characteristics" refers herein to the characteristics which distinguish (i.e., are different) between the new variety and the other cotton variety, such as the Reference Variety, when grown under the same environmental conditions. The distinguishing characteristics between cotton variety FM 2498GLT and cotton variety FM 1911GLT are described herein and also can be seen in Table 2. When comparing cotton variety FM 2498GLT with different varieties, the distinguishing characteristics may therefore include at least one, two, or more (or all) of the characteristics listed in Table 1.

Cotton variety FM 2498GLT has the following distinguishing characteristics when compared to Reference Variety, FM 1911GLT as shown in Table 2: 1) stronger fiber; 2) coarser fiber (micronaire); 3) taller mature plant (from cotyledonary node to terminal); 4) a spreading plant habit; 5) an indeterminate growth; 6) longer length from cotyledonary node to $1^{st}$ fruiting branch; 7) higher gin turnout (stripped); and 8) more seeds per boll, when grown under the same environmental conditions.

Thus, a cotton plant "comprising the distinguishing characteristics of cotton variety FM 2498GLT" (such as a progeny plant) refers herein to a plant which does not significantly differ from said variety in the distinguishing characteristics above. Therefore, in one aspect, a plant (such as a progeny plant of cotton variety FM 2498GLT) is provided which does not significantly differ from cotton variety FM 2498GLT in the distinguishing characteristics above.

Similarity and differences between two different plant lines or varieties can be determined by comparing the number of morphological and/or physiological characteristics (e.g., the characteristics listed in Table 1) that are the same or that are different between the two plant lines or varieties when grown under the same environmental conditions.

"Allele" refers to any one or more alternative forms of a gene locus, all of which alleles relate to one trait or characteristic. In a diploid cell or organism, two alleles of a given gene occupy corresponding loci on a pair of homologous chromosomes.

"Backcrossing" refers to the process in breeder repeatedly crosses hybrid progeny, for example a first generation hybrid ($F_1$), back to one of the parents of the hybrid progeny. Backcrossing can be used to introduce one or more single locus conversions from one genetic background into another.

"Cm to FFB" refers to the measure of centimeters to first fruiting branch.

"Crossing" refers to the mating of two parent plants.

"Cross-pollination" refers to fertilization by the union of two gametes from different plants.

"Desired agronomic characteristics" refers to yield, maturity, pest resistance and lint percent among others (vary from crop to crop and plant to plant), which are desired in a commercially acceptable crop or plant. For example, improved agronomic characteristics for cotton include yield, maturity, fiber content, and fiber qualities.

"Diploid" refers to a cell or organism having two sets of chromosomes.

"Disease resistance" refers to the ability of plants to restrict the activities of a specified pest, such as insect, fungus, virus, or bacterial.

"Disease tolerance" refers to the ability of plants to endure a specified pest (e.g., insect, fungus, virus or bacteria) or an adverse environmental condition and still perform and produce in spite of this disorder.

"Donor parent" refers to the parent of a variety which contains the gene or trait of interest which is desired to be introduced into a second variety.

"E1" refers to elongation, a measure of fiber elasticity (i.e., high=more elastic).

"Emasculate" refers to the removal of plant male sex organs or the inactivation of the organs with a cytoplasmic or nuclear genetic factor conferring male sterility or a chemical agent.

"F1 Hybrid" refers to the first generation progeny of the cross of two non-isogenic plants.

"Fallout (Fo)" refers to the rating of how much cotton has fallen on the ground at harvest.

"FB5 cm to FFN" refers to the measure of centimeters from main stem to first fruiting node at fruiting branch 5.

"Fiber characteristics" refers to the fiber qualities such as strength, fiber length, micronaire, fiber elongation, uniformity of fiber and amount of fiber.

"Length" refers to the fiber length in inches using a (High Volume Instrumentation) HVI.

"Fiber span length" refers to the distance spanned by a specific percentage of fibers in a test specimen, where the initial starting point of the scanning in the test is considered 100 percent as measured by a digital fibergraph.

"2.5% Fiber span length" refers to the longest 2.5% of a bundle of fibers expresses in inches as measured by a digital fibergraph.

"Fiber elongation" or "E1" refers to the elongation of the fiber at the point of breakage in the strength determination as measured by HVI.

"Fiber strength (Str)" refers to the force required to break a bundle of fibers. Fiber strength is expressed in grams per tex on an HVI.

"Fruiting nodes" refers to the number of nodes on the main stem from which arise branches that bear fruit or boll in the first position.

"Genotype" refers to the genetic constitution of a cell or organism.

"Gin turnout" refers to the fraction of lint in a machine harvested sample of seed cotton (e.g., lint, seed, and trash).

"Haploid" refers to a cell or organism having one set of the two sets of chromosomes in a diploid.

"Linkage" refers to a phenomenon wherein alleles on the same chromosome tend to segregate together more often than expected by chance if their transmission was independent.

"Lint index" refers to the weight of lint per seed in milligrams.

"Lint percent" refers to the percentage of the seed cotton that is lint, handpicked samples.

"Lint yield" refers to the measure of the quantity of fiber produced on a given unit of land, presented in pounds of lint per acre.

"Lint/boll" refers to the weight of lint per boll.

"Maturity rating" refers to a visual rating near harvest on the amount of open boils on the plant. The rating ranges from 1 to 5, 1 being early and 5 being late.

"Micronaire (Mic)" refers to a measure of fiber fineness (i.e., high=coarse fiber) as measured with an HVI machine. Within a cotton cultivar, micronaire is also a measure of maturity. Micronaire differences are governed by changes in perimeter or in cell wall thickness, or by changes in both. Within a variety, cotton perimeter is fairly consistent, and maturity will cause a change in micronaire. Consequently, micronaire has a high correlation with maturity within a variety in cotton.

"Mr" refers to fiber maturity ratio.

"Phenotype" refers to the detectable characteristics of a cell or organism, which characteristics are the manifestation of gene expression.

"Plant height" refers to the average height in meters of a group of plants.

"Plant part" includes any part of a plant, such as a plant organ, a plant cell, a plant protoplast, a plant cell tissue culture or a tissue culture from which a whole plant can be regenerated, a plant cell that is intact in a plant, plant callus, vegetative propagation, a leaf, a part of a leaf, pollen, an ovule, an embryo, a meristem, a petiole, a shoot or a part thereof, a stem or part thereof, a root or a part thereof, a root tip, a seed, a part of a seed, a pod, a hypocotyl, cotyledon, a pistil, an anther, and a flower or part thereof and the like. Also, any developmental stage is included, such as seedling, mature plants or leaves.

"Progeny" refers to a plant obtained from a plant designated FM 2498GLT. A progeny may be obtained by regeneration of cell culture or tissue culture or parts of a plant of said variety or by producing the seeds of a plant of said variety. In further aspects, progeny may also encompass plants obtained from crossing of at least one plant of said variety with another cotton plant. A progeny may compromise a mutation or a transgene.

"Quantitative Trait Loci (QTL)" refers to genetic loci that control to some degree numerically representable traits that are usually continuously distributed.

"Recurrent parent" refers to the repeating parent (variety) in a backcross breeding program. The recurrent parent is the variety into which a gene or trait is desired to be introduced.

"Regeneration" refers to the development of a plant from tissue culture.

"Resistance" and "tolerance" are used interchangeably to describe plants that show no symptoms or significant reduced symptoms to a specified biotic pest, pathogen, abiotic influence or environmental conditions compared to a susceptible plant.

"Seed/boll" refers to the number of seeds per boll, handpicked samples.

"Seed cotton/boll" refers to the weight of seed cotton per boll, handpicked samples.

"Seed weight" refers to the weight of 100 seeds in grams.

"Self-pollination" refers to the transfer of pollen from the anther to the stigma of the same plant or a plant of the same genotype.

"Single Locus Converted (Conversion) Plant" refers to plants which are developed by traditional breeding techniques e.g., backcrossing, or via genetic engineering or through mutation breeding, wherein essentially all of the desired morphological and physiological characteristics of the parent variety are recovered, in addition to the one or more genes transferred into the parent via e.g., backcrossing technique. A single locus may comprise one gene, or in the case of transgenic plants, one or more transgenes integrated into the host genome at a single site (locus). It is understood that only the addition of a further characteristic (e.g., addition of gene conferring a further characteristic, such as a disease resistance gene), but also the replacement/modification of an existing characteristic by a different characteristic is encompassed herein.

"Stringout rating" also sometimes referred to as "Storm Resistance" refers to a visual rating prior to harvest of the relative looseness of the seed cotton held in the boll structure on the plant. The rating values are from 1 to 5 (tight to loose in the boll).

"Substantially equivalent" refers to a characteristic that, when compared, does not show a statistically significant difference (e.g., p=0.05) from the mean.

"T1" refers to a measure of fiber strength, grams per tex (high=stronger fiber).

"Tissue Culture" refers to a composition comprising isolated cells of the same or a different type or a collection of such cells organized into parts of a plant. Tissue culture of various tissues of cotton and regeneration of plants therefrom is well known and widely published (see, e.g., Rajasekaran, et., al., (2001), NH: Science Publishers, 269-290). Similarly, methods of preparing cell cultures are known in the art.

"Transgene" refers to a genetic locus comprising a sequence which has been introduced into the genome of a cotton plant by transformation.

"Uniformity ratio (Ur)" refers to the proportion of uniform length fibers. The uniformity ratio is determined by dividing the 50% fiber span length by the 2.5% fiber span length.

"USDA descriptors" are the plant variety descriptors for cotton (*Gossypium* spp.), as published by the US Department of Agriculture, Agricultural Marketing Service, Plant Variety Protection Office, Beltsville, Md. 2075, and which can be downloaded form the worldwide web at ams.usda.gov. under services/plant-variety-protection/pvpo-c-forms under cotton.

"Vegetative Nodes" refer to the number of nodes from the cotyledonary node to the first fruiting branch on the main stem of the plant.

"Vegetative propagation" or "vegetative reproduction" are used interchangeably herein and refer to the method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

DETAILED DESCRIPTION OF THE DISCLOSURE

The disclosure relates to a plant of cotton variety FM 2498GLT, wherein a representative sample of seeds of said variety will be deposited under Budapest Treaty, with ATCC Accession Number PTA 126942.

The disclosure also relates to a seed of cotton variety FM 2498GLT, wherein a representative sample of said seed will be deposited under Budapest Treaty, with ATCC Accession Number PTA 126942.

The disclosure also provides a method of producing cotton seed, comprising the steps of using the plant grown from seed of cotton variety FM 2498GLT, of which a representative sample of seed of said variety will be deposited under Accession Number PTA 126942, as a recurrent parent in crosses with other cotton plants different from cotton variety FM 2498GLT, and harvesting the resultant cotton seed.

The disclosure further provides a plant grown from the seed of cotton variety FM 2498GLT.

Also provided is a plant part obtained from cotton variety FM 2498GLT, wherein said plant part is a leaf, a part of a leaf, pollen, an ovule, a cell, an embryo, a meristem, a petiole, a shoot or a part thereof, a stem or part thereof, a root or a part thereof, a root tip, a seed, a part of a seed, a pod, a hypocotyl, cotyledon, a pistil, an anther, and a flower or part thereof and the like. In another aspect, the plant part obtained from cotton variety FM 2498GLT is a cell or tissue culture.

The disclosure further relates to a cotton variety FM 2498GLT, which when compared to its Reference Variety, FM 1911GLT, has the following distinguishing characteristics as shown in Table 2: 1) stronger fiber; 2) coarser fiber (micronaire); 3) taller mature plant (from cotyledonary node to terminal); 4) a spreading plant habit; 5) an indeterminate growth; 6) longer length from cotyledonary node to $1^{st}$ fruiting branch; 7) higher gin turnout (stripped); and 8) more seeds per boll, when grown under the same environmental conditions. Also encompassed are parts of that plant.

In one aspect, a plant of cotton variety FM 2498GLT or a progeny thereof, comprises all of the following morphological and/or physiological characteristics as shown in Table 1, when grown under the same environmental conditions. A part of this plant is also provided.

In another aspect, cotton variety FM 2498GLT contains a transgene which confers resistance to herbicides glyphosate and glufosinate, and for lepidopteran insect control, referred to in the aggregate as the trait package GLYTOL® TWIN-LINK® (GLT).

In another aspect, the plant of cotton variety FM 2498GLT or a part thereof, or progeny thereof comprises resistance to *Xanthomonas axonopodis* (Bacterial Blight) Race 18, *Verticillium dahlia*, *Helicoverpa* spp. (Bollworm); *Spodoptera frugiperda* (Fall Armyworm), *Pectinophora gossypiella* (Pink Bollworm), and *Heliothis virescens* (Tobacco Bud Worm).

The disclosure further provides a cotton plant which does not significantly differ from the physiological and morphological characteristics of the plant of variety FM 2498GLT, when grown under the same environmental conditions. In a particular aspect, the plants are measured in the same trial (e.g., the trial is conducted as recommended by USDA). The disclosure comprises a part of said plant.

The disclosure also provides for a tissue or cell culture comprising regenerable cells of cotton variety FM 2498GLT. The cell of cotton variety FM 2498GLT used to start the culture can be selected from any plant part suitable for vegetative reproduction, or, in a particular aspect, can be one or more of an embryo, a meristem, a cotyledon, a hypocotyl, pollen, a leaf, an anther, a root, a root tip, a pistil, a petiole, a flower, a fruit, a seed, a pod, or a stem. In another particular aspect, the tissue culture does not contain somaclonal variation or has reduced somaclonal variation. The skilled person is familiar with methods to reduces or prevent somaclonal variation including regular initiation.

In one aspect, the disclosure provides a cotton plant regenerated from the tissue culture or cell culture of variety FM 2498GLT, wherein the regenerated plant has all or all but one, two, or three of the physiological and morphological characteristics of cotton variety FM 2498GLT (or all or all but one, two, or three of the physiological and morphological characteristics as listed in Table 1), when grown under the same environmental conditions. Optionally, the plant has one, two, or more of the physiological and morphological characteristics that are affected by mutation or transformation.

Cotton variety FM 2498GLT, or its progeny, or a plant having all the physiological and/or morphological characteristics or all but one, two, or more which are different from those of cotton variety FM 2498GLT, can also be reproduced using vegetative reproduction methods. Therefore, the disclosure provides for a method of producing a plant, or plant part of cotton variety FM 2498GLT, comprising vegetative propagation of cotton variety FM 2498GLT. Vegetative propagation comprises regenerating a whole plant from a plant part of variety FM 2498GLT, from a progeny or from a plant having all the physiological and/or morphological characteristics of said variety.

The disclosure also provides for a vegetatively propagated plant of variety FM 2498GLT (or from progeny of cotton variety FM 2498GLT or from a plant having all but one, two, or three of the physiological and morphological characteristics of that variety), wherein the plant has all of the morphological and physiological characteristics of cotton variety FM 2498GLT, when grown under the same environmental conditions. In another aspect, the propagated plant has all but one, two, or three of the morphological and physiological characteristics of cotton variety FM 2498GLT, when grown under the same environmental conditions.

In another aspect, the disclosure provides a method of producing a cotton plant comprising crossing a plant of variety FM 2498GLT with second cotton plant at least one, selecting a progeny cotton plant from said crossing, and optionally allowing the progeny cotton plant to form seed. Optionally, the progeny is crossed twice, thrice, or four, five, six, or seven times, and allowed to set seed.

In yet another aspect, the disclosure provides a method of producing a cotton plant, comprising selfing a plant of variety FM 2498GLT one or more times, and selecting a progeny cotton plant from said selfing. In one aspect, the progeny retains all the distinguishing characteristics of cotton variety FM 2498GLT, when grown under the same environmental conditions. In a different aspect, the progeny plant comprises all (or all but one, two, or three) of the physiological and morphological characteristics of cotton variety FM 2498GLT of Table 1.

In other aspects, the disclosure provides a method of producing progeny cotton plant of variety FM 2498GLT comprising crossing the plant of variety FM 2498GLT with other, different or distinct cotton plant, and further selfing or crossing these progeny cotton plant with other, distinct plant and subsequent selection of derived progeny cotton plant. The process of crossing cotton variety FM 2498GLT derived progeny plants with itself or other distinct cotton plants and the subsequent selection in the resulting progenies can be repeated up to 7 or 8 times in order to produce cotton variety FM 2498GLT derived cotton plants. In particular, the disclosure provides for a progeny plant that retains all the essential morphological and physiological characteristics of cotton variety FM 2498GLT, or in another aspect, a progeny plant that retains all, or all but one, two or three of the morphological and physiological characteristics as listed in Table 1, when grown under the same environmental conditions.

Also provided is a method of producing a hybrid cotton variety, comprising repeatedly crossing plants of cotton variety FM 2498GLT with plants of a different variety or varieties or with plants of a non-released line or lines. In practice, three different types of hybrid varieties may be produced (see, e.g., Briggs and Knowles, Chapter 18, supra). The "single cross hybrid" produced by two different lines, the "three-way hybrid", produced by three different lines such that first the single hybrid is produced by using two out of the three lines followed by crossing this single hybrid with the third line, and the "four-way hybrid" produced by four different lines such that first two single hybrids are produced using the lines two by two, followed by crossing the two single hybrids so produced. Each single, three-way or four-way hybrid variety so produced and using cotton variety FM 2498GLT as one of the parent lines contains an essential contribution of variety FM 2498GLT to the resulting hybrid variety is encompassed.

The morphological and/or physiological differences between two different individual plants described herein (e.g., between cotton variety FM 2498GLT and its progeny) or between a plant of variety FM 2498GLT or progeny of said variety, or a plant having all or all but one, two or three of the morphological and physiological characteristics of cotton variety FM 2498GLT, (or all, or all but one, two or three of the characteristics as listed in Table 1) and another known variety can easily be established by growing said variety next to each other or next to the other variety (in the same field, under the same environmental conditions), preferably several locations which are suitable for cotton cultivation, and measuring the morphological and/or physiological characteristics of a number of plants. Thus, the disclosure comprises cotton plant having one, two or three physiological and/or morphological characteristics which are different from those of the plant of variety FM 2498GLT and which otherwise has all the physiological and morphological characteristics of the plant of variety FM 2498GLT, when grown under the same environmental conditions. In another aspect, the different characteristic(s) is/are result of breeding with cotton variety FM 2498GLT and selection of progeny cotton plant comprising one, two or three characteristics which are different that in cotton variety FM 2498GLT. In another aspect, the different characteristic is the result of mutation (e.g., spontaneous mutation or a human induced mutation through e.g., targeted mutagenesis or traditional mutagenesis such as chemically or radiation induced mutagenesis), or it is the result of transformation.

The disclosure provides for methods of producing plants which retain all (or all but one, two or three) of the morphological and physiological characteristics of the plant described herein, but which are still genetically closely related to cotton variety FM 2498GLT. The relatedness can, for example, be determined by fingerprinting techniques (e.g., making use of isozyme markers and/or molecular markers such as SNP markers, amplified fragment length markers (AFLP) markers, microsatellites, minisatellites, random amplified polymorphic DNA (RAPD) markers, restriction fragment length polymorphism (RFLP) markers and others). A plant is "closely related" to cotton variety FM 2498GLT if its DNA fingerprint is at least 80%, 90%, 95% or 98% identical to the fingerprint of that variety. In another aspect, AFLP markers are used for DNA fingerprinting (see, e.g., Vos et al., 1995, Nucleic Acid Research 23: 4407-4414). A closely related plant may have a Jaccard's Similarity index of at least about 0.8, preferably at least about 0.9, 0.95, 0.98 or more (see, e.g., Pisanu et al. ISHS 2004, Acta Hort. 660).

By crossing and/or selfing, single traits may be introduced into cotton variety FM 2498GLT (e.g., using backcrossing scheme), while retaining the remaining morphological and physiological characteristics of said variety and/or retaining one or more or all distinguishing characteristics. A single trait converted plant may thereby be produced. A single locus may comprise one gene, or in the case of transgenic plants, one or more transgenes integrated into the host genome at a single site (locus). For example, disease resistance genes may be introduced, genes responsible for one or more quality traits, yield, etc.

Any pest or disease resistance genes may be introduced into a plant of variety FM 2498GLT, progeny of said variety or into a plant comprising one, two or three of the morphological and physiological characteristics of cotton variety FM 2498GLT (e.g., as listed in Table 1). Resistance to one or more the following diseases or pests may be introduced into the plants described herein: *Alternaria macrospora*, Anthracnose, Ascochyta Blight, *Xanthomonas axonopodis* (Bacterial Blight) Race 1, Race 2, and/or Race 18, Diplodia Boll Rot, Fusarium Wilt, Phymatotrichum Root Rot, *Pythium* spp., Cotton seedling disease (*Rhizoctonia solani*), Southwestern Cotton Rust, *Thielayiopsis basicola*, Verticillium Wilt (*Verticillium dahliae*), *Meloidogyne* spp. (Root-Knot Nematode), Boll Weevil, Bollworm (*Helicoverpa* spp), Cotton Aphid (*Aphis gossypii*), Cotton Fleahopper, Cotton Leafworm, Cutworm, *Spodoptera frugiperda* (Fall Armyworm), Reniform Nematode, Grasshopper, *Lygus*, *Pectinophora gossypiella* (Pink Bollworm), Cotton Spider Mite (*Tetranychus* spp.), Cotton Whitefly (*Bemisia tabaci*), Stink Bug, Tobacco Thrips (*Thrips tabaci*), and/or *Heliothis virescens* (Tobacco Bud Worm). Other resistances, against pathogenic viruses, fungi, bacteria, nematodes, insects or other pests may also be introduced, or other traits.

In one aspect, the disclosure relates to a plant of cotton variety FM 2498GLT comprising at least a first transgene, wherein the cotton plant otherwise has all the physiological and morphological characteristics of the cotton variety FM 2498GLT as listed in Table 1. In a particular aspect, a plant comprising a single locus conversion is provided. A single locus conversion may comprise a transgenic gene which has been introduced by genetic transformation into the cotton variety FM 2498GLT or a progenitor thereof. In a particular aspect, the single locus conversion confers male sterility, herbicide tolerance, insect resistance, pest resistance, disease resistance, modified fatty acid metabolism, modified carbohydrate metabolism, or modified cotton fiber characteristics.

The disclosure provides for a method of introducing a single locus conversion into cotton variety FM 2498GLT comprising:

a) crossing the FM 2498GLT plants, grown from seed deposited under Accession Number PTA 126942, with plants of another cotton line that comprise a desired single locus to produce F1 progeny plants;

b) selecting F1 progeny plants that have the single locus to produce selected F1 progeny plants;

c) crossing the selected F1 progeny plants with the FM 2498GLT plants to produce first backcross progeny plants;

d) selecting for first backcross progeny plants that have the desired single locus and the physiological and morphological characteristics of cotton variety FM 2498GLT as listed in Table 1, when grown under the same environmental conditions, to produce selected first backcross progeny plants; and e) repeating steps c) and d) one or more times (e.g., one, two, three, four, etc. times) in succession to produce selected third or higher backcross progeny plants that comprise the desired single locus and all of the physiological and morphological characteristics of cotton variety FM 2498GLT as listed in Table 1, when grown under the same environmental conditions.

Plants produced by this method have all of the physiological and morphological characteristics of cotton variety FM 2498GLT, except for the characteristics derived from the desired trait.

In one aspect, a plant of cotton variety FM 2498GLT may also be mutated and mutated seeds or plants may be selected in order to change one or more characteristics of said variety. Similarly, cotton variety FM 2498GLT may be transformed and regenerated, whereby one or more chimeric genes are introduced into the variety or into a plant comprising one, two or three of the physiological and morphological characteristics (e.g., as listed in Table 1). Transformation can be carried out using methods well known in the art, such as *Agrobacterium tumefaciens* mediated transformation or biolistics, followed by selection of the transformed cells and regeneration into plants (see, e.g., Sakhanokho et al., 2004, Reynaerts et al., 2000, Umbeck et al., 1988). Examples of transgenic events transformed in this way are "LLCotton25," USDA-APHIS petition 02-042-01p, "Cot 102," USDA-APHIS petition 03-155-01p, and "281-24-236," USDA-APHIS petition 03-036-01p combined with "3006-210-23," USDA-APHIS petition 03-036-02p. Information regarding these and other transgenic events referred to herein may be found at the U.S. Department of Agriculture's (USDA) Animal and Plant Health Inspection Service (APHIS) website (www.aphis.usda.gov/aphis/home/). An "Event" is defined as a (artificial) genetic locus that, as a result of genetic engineering, carries a foreign DNA comprising at least one copy of the gene(s) of interest. Other methods of genetic transformation are well known in the art such as microprojectile bombardment (see, e.g., U.S. 2009/0049564).

In another aspect, a desired trait (e.g., gene(s) conferring pest or disease resistance, herbicide, fungicide or insecticide tolerance, etc.) can be introduced into cotton variety FM 2498GLT, or progeny of said variety, by transforming said variety or progeny of said variety with a transgene that confers the desired trait, wherein the transformed plants retains all or all but one, two or three of the physiological and/or morphological characteristics of cotton variety FM 2498GLT or the progeny of the said and contains the desired trait.

The disclosure also provides for a method of producing a cotton plant comprising introducing a transgene conferring the desired trait into the plant, resulting in a plant with the desired trait and all or all but one, two or three of the physiological and morphological characteristics of cotton variety FM 2498GLT, when grown under the same environmental conditions. In another aspect, the disclosure provides for a method of producing a cotton plant from cotton variety FM 2498GLT comprising genetically transforming a desired trait in regenerable cell or tissue culture from a plant described herein, resulting in a cotton plant that retains all the physiological and morphological characteristics of cotton variety FM 2498GLT, except for the characteristics changed by the introduction of the desired trait.

In a further aspect, the desired trait is modified cotton fiber characteristics, herbicide resistance, insect or pest resistance, disease resistance, including bacterial or fungal disease resistance, male sterility, modified carbohydrate metabolism and/or modified fatty acid metabolism. Such traits and genes conferring such traits are known in the art (see, e.g., US 2009/0049564).

In a particular aspect, the desired trait is herbicide tolerance and the tolerance is linked to a herbicide such as glyphosate, glufosinate, sulfonylurea, dicamba, phenoxy proprionic acid, cyclohexanedione, triazine, benzonitrile, bromoxynil or imidazalinone.

In another particular aspect, the desired trait is insect resistance conferred by a transgene encoding a *Bacillus thuringiensis* (Bt) endotoxin, a derivative thereof, or a synthetic polypeptide modeled thereon.

The disclosure also provides for a method of producing an inbred cotton plant derived from the cotton variety FM 2498GLT comprising:

a) preparing a progeny plant derived from cotton variety FM 2498GLT, a representative sample of seed of said variety will be deposited under ATCC Accession Number PTA 126942, by crossing cotton variety FM 2498GLT with a cotton plant of a second variety;

b) crossing the progeny plant with itself or a second plant to produce a seed of a progeny plant of a subsequent generation;

c) growing a progeny plant of a subsequent generation from said seed and crossing the progeny plant of a subsequent generation with itself or a second plant; and d) repeating steps (b) and (c) for an additional 3-10 generations with sufficient inbreeding to produce an inbred cotton plant derived from the cotton variety FM 2498GLT.

The disclosure also provides for cotton lint or fiber produced by cotton variety FM 2498GLT. Also provided is the textile produced from the unique fiber of cotton variety FM 2498GLT.

The disclosure also provides for a method of producing a commodity plant product (e.g., lint, cotton seed oil, seed), comprising obtaining a plant of cotton variety FM 2498GLT or a part thereof, and producing said commodity plant product therefrom.

All documents (e.g., patent publications, non-patent literature) are herein incorporated by reference in their entirety.

US Department of Agriculture, Agricultural Marketing Service, "Objective Description of Variety Cotton (*Gossypium* spp.)", world wide web at ams.usda.gov/services/plant-variety-protection/pvpo-c-forms, under cotton.

Briggs, F. N., and Knowles, P. F., "Introduction to Plant Breeding", Rheinhold Publishing Corporation, 1967.

Burdett, L. P., "Cotton Variety 02T15," U. S. Pub. No. 20090049564.

Pisanu, A. B., et. al., "Yield and Biometric Characteristics of 9 Clones Selected from the Population of "*Spinoso sardo*" Artichokes, Acta Hort., 2004, ISHS 660, pp. 83-89.

Reynaerts, et. al., "Improved Method for *Agrobacterium* Mediated Transformation of Cotton," 2000, Patent application number WO 0071733.

Sakhanoko, H. F., et. al., "Induction of Somatic Embryogenesis and Plant Regeneration in Select Georgia and Pee Dee Cotton Lines", Crop Science, 2004, vol. 44, pp. 2199-2205.

Stam, P., "Marker-assisted introgression: speed at any cost?" Proceedings of the Eucarpia Meeting on Leafy Vegetable Genetics and Breeding, Noordwijkerhout, The Netherlands, 19-21 Mar. 2003. Eds. Th. J. L. van Hintum, A. Lebeda, D. Pink, J. W. Schut. P117-124.

Trolinder, et al., "Herbicide Tolerant Cotton Plants having Event EE-GH1," 2004, U.S. Pat. No. 6,818,807

Umbeck, et. al., "Genetic Engineering of Cotton Plants and Lines", Patent application number EP0290355.

Vos, P., et al., "AFLP: A New Technique for DNA Fingerprinting", Nucleic Acids Research, 1995, vol. 23(21), pp. 4407-4414.

Deposit Information

A total of 2500 seeds of variety FM 2498GLT have been deposited and approved according to the Budapest Treaty by the Applicant on Jan. 7, 2021 at the American Type Culture Collection (ATCC), 1801 University Boulevard, Manassas, Va. 20110, USA. The deposit has been assigned ATCC Accession Number PTA 126942. Seed of cotton variety FM 2498GLT is located at the BASF Maricopa Cotton Breeding Station, 880 N Power Road, Bapschule, Ariz. 85121, with lot number XB7AR6138F.

Access to this deposit will be available during the pendency of the application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon granting of the patent. The deposit will be maintained for a period of 30 years, or 5 years after the most recent request, or for the enforceable life of the patent, whichever is longer, and will be replaced if it becomes nonviable during that period. Applicant does not waive any rights granted under this patent or under the Plant Variety Protection Act (7 U.S.C. § 2321 et seq.).

Development of Cotton Variety FM 2498GLT

The disclosure described herein has been obtained by a general breeding process comprising the steps outlined below (see, e.g., Introduction to Plant Breeding, 1967, Chapter 11, Briggs and Knowles, Rheinhold Publishing Corporation).

Parent plants, which have been selected for good agronomic and fiber quality traits are manually crossed in different combinations. The resulting F1 (Filial generation 1) plants are self-fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested, and the bolls analyzed for fiber characteristics and the seed cleaned and stored. This procedure is repeated in the following growing seasons, whereby the selection and testing units increase from individual plants in the F2, to multiple plant containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analysis of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary the procedure described above, such as by accelerating the process by testing a particular line earlier or retesting a line another year. He may also select plants for further crossing with existing parent plants or with other plants resulting from the current selection procedure.

By the method of recurrent backcrossing, (see, e.g., Briggs and Knowles, supra, in chapter 13, "The Backcross Method of Breeding"), the breeder may introduce a specific trait or traits into an existing valuable line or variety, while otherwise preserving the unique combination of characteristics of this line or variety. In this crossing method, the valuable parent is recurrently used to cross it at least two or three times with each resulting backcross F1, followed by selection of the recurrent parent plant type, until the phenotype of the resulting F1 is similar or almost identical to the phenotype of the recurrent parent with the addition of the expression of the desired trait or traits.

Cotton variety FM 2498GLT was derived from a backcross breeding program with a proprietary recurred line as one parent and a proprietary line as the donor parent which contained GLYTOL® and TWINLINK® proprietary technologies, which expresses tolerance to herbicides. The initial cross between the proprietary recurrent line and the proprietary GLYTOL® and TWINLINK® donor line was made in the greenhouse. Two generations of backcrosses to the proprietary recurrent line were then performed. Individual plants were selected for homozygosity in the BC2F2 generation. The following year, BC2F3 progeny rows were grown for seed increase. Then sister lines of this material were tested in several locations across the High Plains of Texas. Two lines were identified bases upon data gathered from replicated testing. These two lines were selected and bulked based upon performance and adaptations to the Texas High Plains.

Characteristics of Cotton Variety FM 2498GLT

The most similar variety to cotton variety FM 2498GLT is referred to as FM 1911GLT, a variety from BASF Agricultural Solutions Seed US LLC. In Table 1, a comparison between cotton varieties FM 2498GLT and FM 1911GLT is shown based on a trial in the USA. In Table 2, the distinguishing characteristics between cotton variety FM 2498GLT and the Reference Variety FM 1911GLT is shown.

In one aspect, the disclosure provides a plant having all the physiological and morphological characteristics of cotton variety FM 2498GLT as presented in Table 1.

TABLE 1

Objective Description of Cotton Variety FM 2498GLT and the Reference Variety FM 1911GLT

| USDA Descriptors | FM 2498GLT | FM 1911GLT |
|---|---|---|
| Areas of Adaptation: | | |
| Adapted | | |
| Not Adapted | | |
| Not tested | | |
| Eastern | Not tested | Not tested |
| Delta | Not tested | Not tested |
| Central | Not tested | Not tested |
| Blacklands | Not tested | Not tested |
| Plains | Adapted | Adapted |
| Western | Not tested | Not tested |
| Arizona | Not tested | Not tested |
| San Joaquin | Not tested | Not tested |
| Other | | |
| General Plant Type: | | |
| Plant habit: spreading, intermediate, compact | Spreading | Intermediate |
| Foliage: sparse, intermediate, dense | Intermediate | Intermediate |
| Stem lodging: lodging, intermediate, erect | Erect | Erect |
| Fruiting branch: clustered, short, normal | Normal | Normal |
| Growth: determinate, intermediate, indeterminate | Indeterminate | Intermediate |
| Leaf color: greenish yellow, light green, medium green, dark green | Light green | Light green |
| Boll shape: length less than width, length equal to width, length more than width | Length more than width | Length more than width |
| Boll breadth: broadest at base, broadest at middle | Broadest at middle | Broadest at middle |
| Maturity: | | |
| Days till maturity: | Mid maturity | Early-mid maturity |
| Plant: | | |
| cm to 1$^{st}$ fruiting branch: (from cotyledonary node) | 25.5 | 23.1 |
| No. of nodes to 1$^{st}$ fruiting branch: (excluding cotyledonary node) | 8.0 | 7.9 |
| Mature plant height (cm): (from cotyledonary node to terminal) | 75.2 | 64.2 |
| Leaf: (upper most fully expanded leaf) | | |
| Type: normal, sub okra, okra, super okra | Normal | Normal |
| Pubescence: absent, sparse, medium, dense | Sparse | Sparse |
| Nectaries: present, absent | Present | Present |
| Stem pubescence: glabrous, intermediate, hairy | Intermediate | Intermediate |
| Glands: absent, sparse, normal, more than normal | | |
| Leaf: | Normal | Normal |
| Stem: | Normal | Normal |
| Calyx lobe: (normal is absent) | Normal | Normal |
| Flower: | | |
| Petals: cream, yellow | Cream | Cream |
| Pollen: cream, yellow | Cream | Cream |
| Petal spot: present, absent | Absent | Absent |

TABLE 1-continued

Objective Description of Cotton Variety FM 2498GLT and the Reference Variety FM 1911GLT

| USDA Descriptors | FM 2498GLT | FM 1911GLT |
| --- | --- | --- |
| Seed: | | |
| Seed index: (g/100 seeds, fuzzy basis) | 12.5 | 12.8 |
| Boll: | | |
| Lint percent: | 0.44 | 0.41 |
| picked x | | |
| pulled __ | | |
| Gin turnout: | .375 | .330 |
| picked x | | |
| stripped __ | | |
| Number of seeds per boll: | 28.1 | 26.8 |
| Grams seed cotton per boll: | 3.9 | 3.8 |
| Number of locules per boll: | 4.6 | 4.3 |
| Boll type: | Storm resistant | Storm resistant |
| stormproof, storm resistant, open | | |
| Fiber properties: | | |
| Method: | HVI | HVI |
| Length (inches, 2.5% SL): | 1.17 | 1.18 |
| Uniformity (%): | 79.2 | 79.1 |
| Strength, T1 (g/tex): | 29.4 | 29.0 |
| Elongation, E1 (%): | 8.6 | 8.6 |
| Micronaire: | 3.22 | 2.93 |
| Resistance to diseases: | | |
| Not tested, susceptible, moderately susceptible, moderately resistant, resistant | | |
| Bacterial Blight, Race 18 | Moderately resistant | Moderately resistant |
| *Verticillium* Wilt | Moderately resistant | Moderately resistant |
| Resistance to nematodes, insects and pests: | | |
| Not tested, susceptible, moderately susceptible, moderately resistant, resistant | | |
| Bollworm | Resistant | Resistant |
| Fall Armyworm | Moderately resistant | Moderately resistant |
| Pink Bollworm | Resistant | Resistant |
| Tobacco Bud Worm | Resistant | Resistant |
| Root-knot Nematode | Not tested | Moderately resistant |

TABLE 2

Distinguishing Characteristics Between the Cotton Variety FM 2498GLT and the Reference Variety FM 1911GLT

| Distinguishing Characteristics | FM 2498GLT | FM 1911GLT |
| --- | --- | --- |
| Fiber Strength, T1 (g/tex) | 29.4 | 29.0 |
| Fiber Micronaire | 3.22 | 2.93 |
| Mature Plant Height, cm (from cotyledonary node to terminal) | 75.2 | 64.2 |
| Plant Habit | Spreading | Intermediate |
| Plant Growth | Indeterminate | Intermediate |
| Maturity | Mid maturity | Early-mid maturity |
| cm to 1st Fruiting Branch (from cotyledonary node) | 25.5 | 23.1 |
| Gin Turnout (stripped) | .375 | .330 |
| Number of Seeds per Boll | 28.1 | 26.8 |

The invention claimed is:

1. A plant or regenerable part thereof or seed of cotton variety FM 2498GLT, wherein a representative sample of seed of said cotton variety has been deposited under ATCC Accession No. PTA 126942.

2. The plant part of claim 1, wherein said plant part is a leaf, an ovule, a cell, a root, a flower, or a pod.

3. A plant, or regenerable part thereof, produced by growing the seed of claim 1.

4. A cotton plant having all the morphological and physiological characteristics of the plant of claim 1, wherein a representative sample of seeds of said variety has been deposited under ATCC Accession No. PTA 126942.

5. A cell or tissue culture produced from the plant, or a part thereof, of claim 1.

6. A cotton plant regenerated from the cell or tissue culture of claim 5, wherein said plant has all of the morphological and physiological characteristics of cotton variety FM 2498GLT, when grown under the same environmental conditions, and wherein a representative sample of seed of said cotton variety has been deposited under ATCC Accession Number PTA 126942.

7. A method of producing the plant of claim 1, or a part thereof, comprising vegetative reproduction of the plant of cotton variety FM 2498GLT, wherein a representative sample of seed of said cotton variety has been deposited under ATCC Accession Number PTA 126942.

8. The method of claim 7, wherein said vegetative propagation comprises culturing regenerable cells or tissue from cotton variety FM 2498GLT.

9. A plant, or regenerable part thereof, obtained by vegetative reproduction from the plant, or a part thereof, of claim 1, wherein said plant or a part thereof has all of the morphological and physiological characteristics of cotton variety FM 2498GLT, wherein a representative sample of seed of said cotton variety has been deposited under ATCC Accession Number PTA-126942.

10. A method of producing a F1 hybrid cotton seed, comprising crossing the plant of claim 1 with a different cotton plant and harvesting the resultant F1 hybrid cotton seed.

11. An F1 hybrid cotton seed produced by the method of claim 10.

12. An F1 hybrid cotton plant, or a part thereof, produced by growing the hybrid seed of claim 11.

13. A method of introducing a desired trait into a cotton plant, comprising transforming the plant of claim 1 with a transgene that confers the desired trait, wherein the transformed plant otherwise retains all of the morphological and physiological characteristics of cotton variety FM 2498GLT and contains the desired trait.

14. The method of claim 13, wherein said desired trait is fiber quality, herbicide resistance, insect or pest resistance, disease resistance, bacterial disease resistance, fungal disease resistance, male sterility, modified carbohydrate metabolism, or modified fatty acid metabolism.

15. A method of introducing a desired trait into a cotton plant, comprising transforming the plant of claim 1 with a transgene that confers the desired trait, wherein the transformed plant retains all of the morphological and physiological characteristics of cotton variety FM 2498GLT and contains the desired trait, wherein a representative sample of seed of said cotton variety has been deposited under ATCC Accession Number PTA-126942.

16. A cotton plant produced by the method of claim 15.

17. A method of introducing a single locus conversion into cotton variety FM 2498GLT, comprising:

(a) crossing a plant of variety FM 2498GLT with a second plant comprising a desired single locus to produce F1 progeny plants, wherein the single locus confers male sterility, herbicide tolerance, insect resistance, pest resistance, disease resistance, modified fatty acid metabolism, modified carbohydrate metabolism, or modified cotton fiber characteristics;
(b) selecting F1 progeny plants that have the single locus to produce selected F1 progeny plants;
(c) crossing the selected progeny plants with at least a first plant of variety FM 2498GLT to produce backcross progeny plants;
(d) selecting backcross progeny plants that have the single locus and otherwise comprise all of the physiological and morphological characteristics of cotton variety FM 2498 GLT to produce selected backcross progeny plants; and
(e) repeating steps (c) and (d) one or more times in succession to produce selected second or higher backcross progeny plants that comprise the single locus and otherwise comprise all of the physiological and morphological characteristics of cotton variety FM 2498GLT, when grown under the same environmental conditions, wherein a representative sample of seed of said cotton variety has been deposited under ATCC Accession Number PTA-126942.

18. A method of producing a commodity plant product comprising obtaining the commodity plant product from a plant of cotton variety FM 2498GLT, wherein a representative sample of seed of said cotton variety has been deposited under ATCC Accession Number PTA 126942.

19. The method of claim 18, wherein the commodity plant product is lint, seed oil, or seed.

\* \* \* \* \*

UNITED STATES PATENT AND TRADEMARK OFFICE
CERTIFICATE OF CORRECTION

PATENT NO. : 10,966,384 B2
APPLICATION NO. : 16/405254
DATED : April 6, 2021
INVENTOR(S) : Cory Mills Page 1 of 1

It is certified that error appears in the above-identified patent and that said Letters Patent is hereby corrected as shown below:

On the Title Page

(65) Related U.S. Application Data Reads:
"Continuation-in-part of application No. 16/279,791, filed on December 19, 2019, now abandoned."

Should Read:
--Continuation-in-part of application No. 16/279,791, filed on February 19, 2019, now abandoned.--

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*